US010705014B2

(12) United States Patent
Sakamoto et al.

(10) Patent No.: US 10,705,014 B2
(45) Date of Patent: Jul. 7, 2020

(54) IMAGE DIAGNOSIS APPARATUS, METHOD OF CONTROLLING IMAGE DIAGNOSIS APPARATUS, COMPUTER PROGRAM, AND COMPUTER READABLE STORAGE MEDIUM

(71) Applicant: TERUMO KABUSHIKI KAISHA, Tokyo (JP)

(72) Inventors: Masayuki Sakamoto, Hadano (JP); Isao Mori, Chofu (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days.

(21) Appl. No.: 16/366,252

(22) Filed: Mar. 27, 2019

(65) Prior Publication Data
US 2019/0219496 A1 Jul. 18, 2019

Related U.S. Application Data

(63) Continuation of application No. PCT/JP2017/032097, filed on Sep. 6, 2017.

(30) Foreign Application Priority Data

Sep. 27, 2016 (JP) .................. 2016-188696

(51) Int. Cl.
*G01N 21/21* (2006.01)
*G02F 1/01* (2006.01)
(Continued)

(52) U.S. Cl.
CPC ............... *G01N 21/21* (2013.01); *A61B 1/00* (2013.01); *A61B 1/00045* (2013.01);
(Continued)

(58) Field of Classification Search
CPC .................. G01N 21/21; G01N 21/17; G01N 2021/1787; A61B 1/00; A61B 1/06; A61B 1/00045; A61B 1/00172; A61B 5/0066; G02F 1/0136
See application file for complete search history.

(56) References Cited

U.S. PATENT DOCUMENTS 6,208,421 B1 * 3/2001 Maris ................. G01N 21/1702
356/432
2007/0232891 A1 * 10/2007 Hirota ..................... A61B 8/13
600/407
(Continued)

FOREIGN PATENT DOCUMENTS

JP 5787255 B2 8/2015
WO 2014157645 A1 10/2014

OTHER PUBLICATIONS

International Search Report (PCT/ISA/210) dated Nov. 21, 2017, by the Japan Patent Office as the International Searching Authority for International Application No. PCT/JP2017/032097.
(Continued)

*Primary Examiner* — Dominic J Bologna
(74) *Attorney, Agent, or Firm* — Buchanan Ingersoll & Rooney PC (57) ABSTRACT

An image diagnosis apparatus determines an effective pulse based on a pulse signal corresponding to the rotation of an imaging core from a pulse signal corresponding to an A line indicating a period of a light source and switches the polarization state of light transmitted from an optical transceiver according to the effective pulse. According to the effective pulse, the image diagnosis apparatus acquires a signal of interference light between the light received by the optical transceiver and reference light.

20 Claims, 5 Drawing Sheets

(51) Int. Cl.
*A61B 1/00* (2006.01)
*A61B 5/00* (2006.01)
*G01N 21/17* (2006.01)
*A61B 1/06* (2006.01)

(52) U.S. Cl.
CPC ............ *A61B 1/00172* (2013.01); *A61B 1/06* (2013.01); *A61B 5/0066* (2013.01); *G01N 21/17* (2013.01); *G02F 1/0136* (2013.01); *G01N 2021/1787* (2013.01)

(56) References Cited

U.S. PATENT DOCUMENTS

| | | | | |
|---|---|---|---|---|
| 2007/0244391 | A1* | 10/2007 | Hirota | A61B 5/0066 600/443 |
| 2014/0115022 | A1* | 4/2014 | Yasuno | G01B 9/02044 708/204 |
| 2015/0005627 | A1* | 1/2015 | Itoh | A61B 8/54 600/427 |
| 2016/0022248 | A1* | 1/2016 | Mori | A61B 8/4416 600/427 |
| 2016/0095577 | A1* | 4/2016 | Itoh | A61B 8/4416 600/427 |
| 2016/0299170 | A1* | 10/2016 | Ito | G02B 26/10 |

OTHER PUBLICATIONS

Written Opinion (PCT/ISA/237) dated Nov. 21, 2017, by the Japan Patent Office as the International Searching Authority for International Application No. PCT/JP2017/032097.

\* cited by examiner

FIG. 5

IMAGE DIAGNOSIS APPARATUS, METHOD OF CONTROLLING IMAGE DIAGNOSIS APPARATUS, COMPUTER PROGRAM, AND COMPUTER READABLE STORAGE MEDIUM

CROSS-REFERENCES TO RELATED APPLICATIONS

This application is a continuation of International Application No. PCT/JP2017/032097 filed on Sep. 6, 2017, which claims priority to Japanese Application No. 2016-188696 filed on Sep. 27, 2016, the entire content of both of which is incorporated herein by reference.

FIELD OF THE INVENTION

The present disclosure generally relates to an image diagnostic technique.

BACKGROUND DISCUSSION

Image diagnosis apparatuses are widely used for diagnosis of arteriosclerosis or for preoperative diagnosis at the time of intravascular treatment with a high performance catheter such as a balloon catheter or stent, or for confirming the result after surgery.

An optical coherence tomography diagnostic apparatus (OCT: optical coherence tomography) is one of the imaging apparatuses for diagnosis, and a polarization sensitive OCT is further included in the optical coherence tomography diagnostic apparatus.

The polarization sensitive OCT is for obtaining polarization characteristics of a site to be diagnosed (sample) of a test object. The polarization sensitive OCT obtains the polarization characteristics of the sample based on interference light between reflected light from the sample with respect to a plurality of incident lights having different polarization states and reference light (Japanese Patent No. 5787255).

In the case of switching the polarization state of light from a light source based on a timing (A line trigger) of the same frequency as the light source of wavelength sweeping light, if interference waves are collected according to an A line trigger, corresponding interference waves can be obtained according to switching order of the polarization states of the light. However, the timing (frequency) of collecting interference waves varies, for example, according to the number of collection lines per one revolution of a motor inside a motor drive unit for rotating an imaging core, so in this case, the corresponding interference waves are not necessarily obtained in the switching order of the polarization states of the light.

SUMMARY OF INVENTION

A technique is disclosed for collecting corresponding interference waves in the switching order of polarization states of light in the polarization sensitive OCT.

An image diagnosis apparatus is disclosed, the image diagnosis apparatus including a motor drive unit to which a probe rotatably accommodating an imaging core including an optical transceiver configured to transmit and receive light is connected so that the imaging core is rotated; switching means for determining an effective pulse based on a pulse signal corresponding to the rotation of the imaging core from a pulse signal corresponding to an A line indicating a period of a light source and for switching a polarization state of the light transmitted from the optical transceiver according to the effective pulse; and acquiring means for acquiring a signal of interference light between the light received by the optical transceiver and reference light according to the effective pulse.

According to the present disclosure, it is possible to collect corresponding interference waves in order of switching the polarization state of light in the polarization sensitive OCT.

In accordance with an aspect, an image diagnosis apparatus is disclosed comprising: a motor drive unit configured to be connected to a probe, the probe being configured to rotatably accommodate an imaging core including an optical transceiver configured to transmit and receive light, the motor drive unit being configured to rotate the imaging core; and a processor configured to: determine an effective pulse based on a pulse signal corresponding to the rotation of the imaging core from a pulse signal corresponding to an A line indicating a period of a light source and for switching a polarization state of the light transmitted from the optical transceiver according to the effective pulse; and acquire a signal of interference light between the light received by the optical transceiver and reference light according to the effective pulse.

In accordance with another aspect, a method is disclosed of controlling an image diagnosis apparatus having a motor drive unit configured to be connected to a probe, the probe configured to be rotatably accommodate an imaging core including an optical transceiver configured to transmit and receive light, and wherein the motor drive unit is configured to rotate the imaging core, the method comprising: determining an effective pulse based on a pulse signal corresponding to the rotation of the imaging core from a pulse signal corresponding to an A line indicating a period of a light source and switching a polarization state of the light transmitted from the optical transceiver according to the effective pulse; and acquiring a signal of interference light between the light received by the optical transceiver and reference light according to the effective pulse.

In accordance with an aspect, a non-transitory computer readable medium is disclosed containing a computer program having computer readable code embodied to carry out a method of controlling an image diagnosis apparatus having a motor drive unit configured to be connected to a probe, the probe configured to be rotatably accommodate an imaging core including an optical transceiver configured to transmit and receive light, and wherein the motor drive unit is configured to rotate the imaging core, the method comprising: determining an effective pulse based on a pulse signal corresponding to the rotation of the imaging core from a pulse signal corresponding to an A line indicating a period of a light source and switching a polarization state of the light transmitted from the optical transceiver according to the effective pulse; and acquiring a signal of interference light between the light received by the optical transceiver and reference light according to the effective pulse.

Other features and advantages of the present disclosure will become apparent from the following description with reference to the accompanying drawings. Note that in the accompanying drawings, the same or similar configuration is denoted by the same reference numeral.

BRIEF DESCRIPTION OF THE DRAWINGS

The accompanying drawings are included in the specification, constitute a part of the specification, illustrate embodiments of the present invention, and serve to explain principles of the present invention together with the description.

DESCRIPTION OF EMBODIMENTS

Hereinafter, each embodiment of the present disclosure will be described in detail with reference to the accompanying drawings. Note that since the embodiments described below are preferred specific examples of the present disclosure, various technical limitations are given. However, in the following description, the scope of the present disclosure is not limited to these embodiments unless there is a statement to limit the present disclosure in particular.

First Embodiment

Hereinafter, an embodiment of the present disclosure will be described in detail with reference to the accompanying drawings. Note that the image diagnosis apparatus in the present specification will be described as having a polarization sensitive OCT function.

Figure 1:
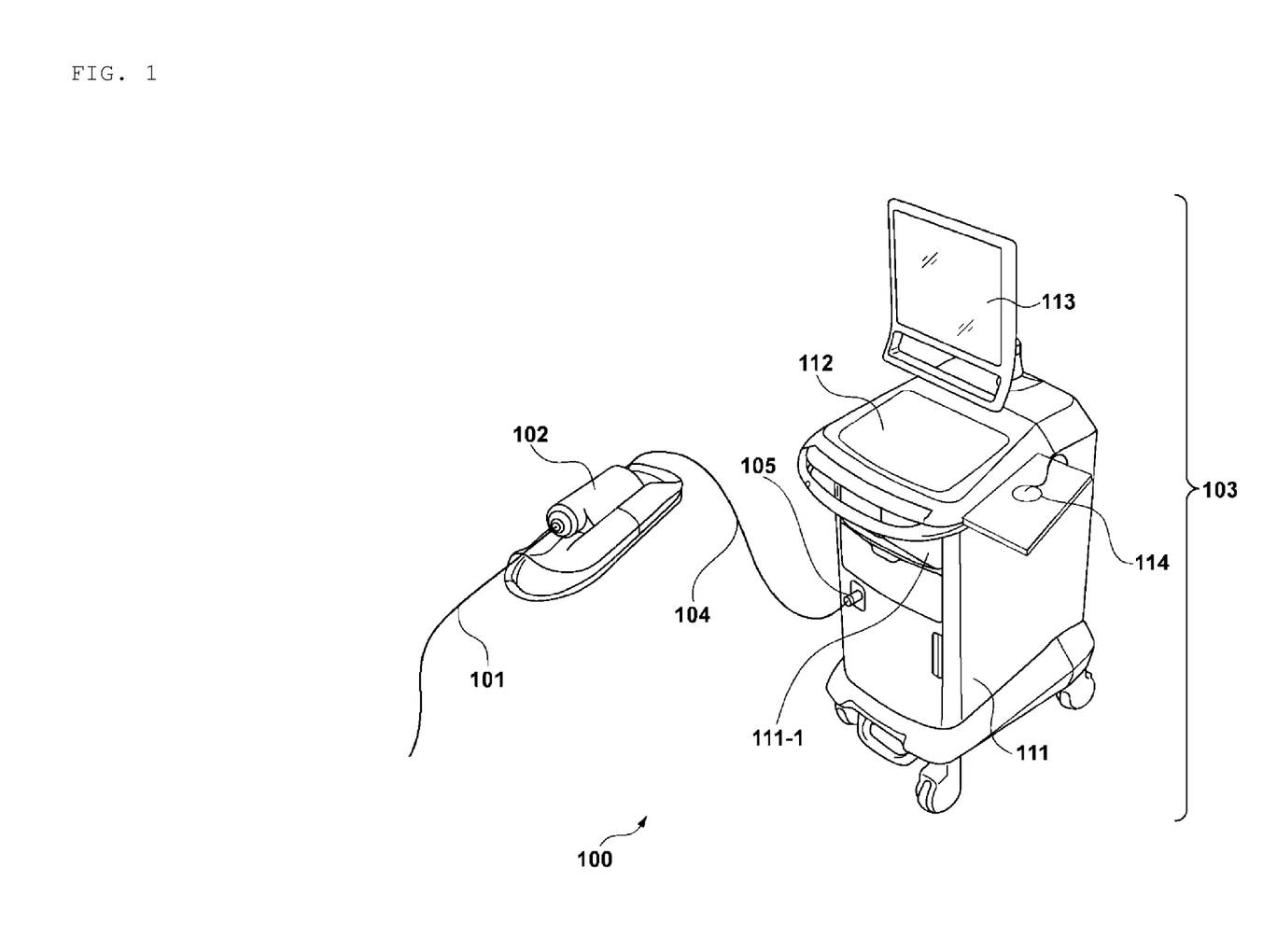
FIG. 1 is a diagram showing an example of an appearance of an image diagnosis apparatus in accordance with an exemplary embodiment.

FIG. 1 is a diagram showing an example of an appearance of an image diagnosis apparatus 100 according to the present embodiment. As shown in FIG. 1, the image diagnosis apparatus 100 includes a probe 101, a pull-back unit 102, and an operation control apparatus 103. The pull-back unit 102 and the operation control apparatus 103 are connected via a connector 105 by a cable 104 accommodating a signal line and an optical fiber.

In accordance with an exemplary embodiment, the probe 101 is directly inserted into a blood vessel, and accommodates a rotatable imaging core which is movable in the longitudinal direction of the probe 101. At a distal end of the imaging core, there is provided an optical transceiver continuously transmitting transferred light (measurement light) into the blood vessel and continuously receiving reflected light from the blood vessel. In the image diagnosis apparatus 100, a state inside the blood vessel is measured by using the imaging core.

The probe 101 is detachably mounted to the pull-back unit 102, and the pull-back unit 102 has a built-in motor that is driven to regulate the axial motion and rotational motion of the imaging core inserted in the probe 101 in the blood vessel. In addition, the pull-back unit 102 functions as a relay device for signals between the optical transceiver in the imaging core and the operation control apparatus 103. That is, the pull-back unit 102 has a function of transmitting the measurement light from the operation control apparatus 103 to the optical transceiver and a function of transmitting the reflected light from a biological tissue detected by the optical transceiver to the operation control apparatus 103.

In accordance with an exemplary embodiment, when measuring, the operation control apparatus 103 has a function for inputting various setting values and a function of processing optical interference data obtained by the measurement and displaying various blood vessel images.

In the operation control apparatus 103, reference numeral 111 denotes a main control unit. The main control unit 111 generates interference light data by causing the reflected light from the imaging core and reference light obtained by separating the light from the light source to interfere with each other and generates line data by performing fast Fourier transform (FFT) on the interference light data. Then, an optical tomographic image is generated through interpolation processing.

In accordance with an exemplary embodiment, reference numeral 111-1 denotes a printer and DVD (digital versatile disc or digital optical disc storage format) recorder, which prints the processing result in the main control unit 111 and writes the result into the DVD, and thereby, outputs data (such as image setting of optical tomographic image, imaging environment, information for specifying imaging target) to the outside. In addition, the printer and DVD recorder (reference number 111-1) can be provided with an interface (not shown) such as USB, and outputs the data to an external storage medium. Reference numeral 112 denotes an operation panel, and a user inputs various setting values and instructions via the operation panel 112. Reference numeral 113 denotes an LCD (liquid crystal display) monitor as a display apparatus, which displays various cross-sectional images generated by the main control unit 111. Reference numeral 114 denotes a mouse as a pointing device (coordinate input device).

Figure 2:
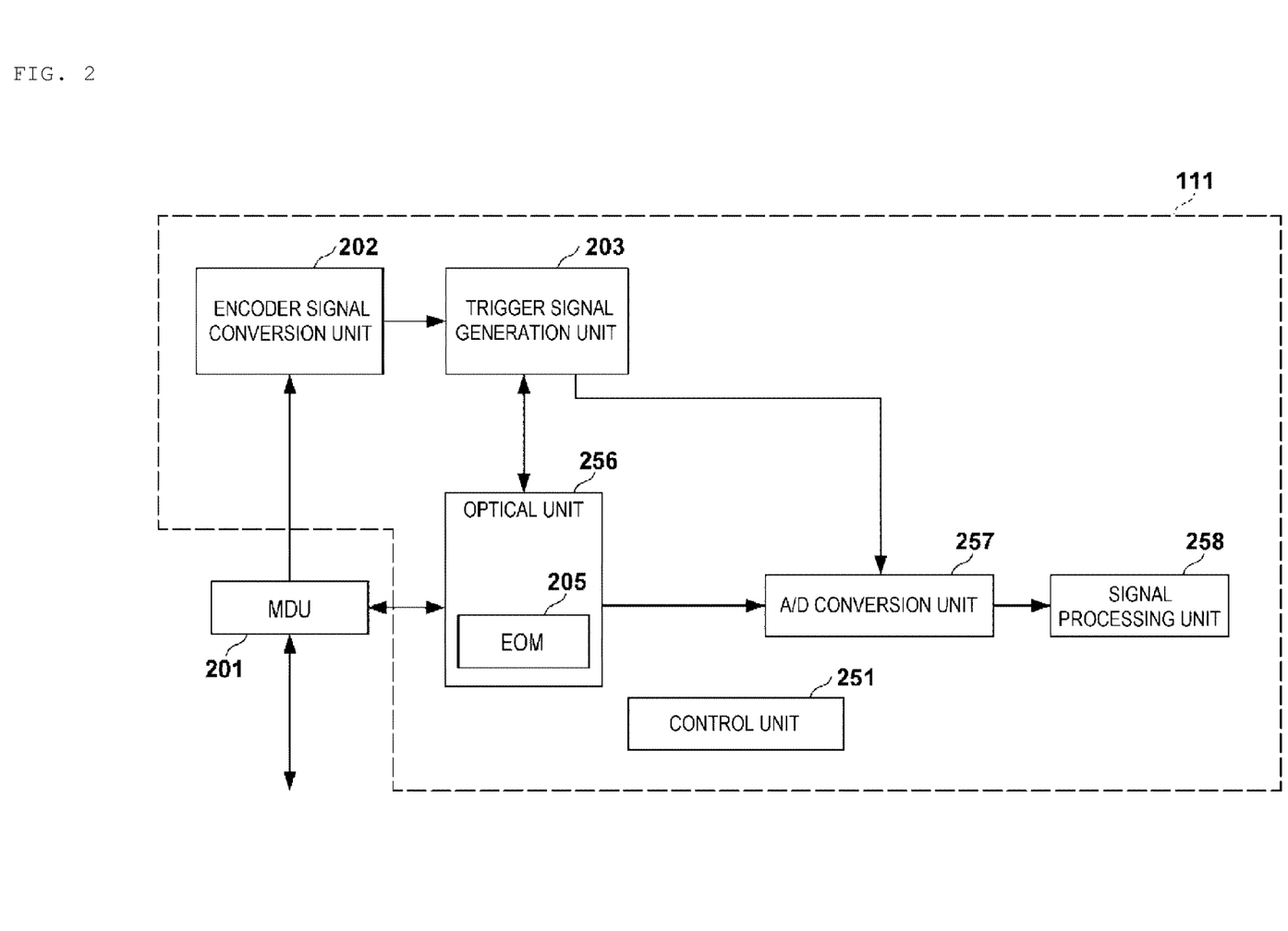
FIG. 2 is a block diagram showing a configuration example of a main control unit in accordance with an exemplary embodiment.

Next, a configuration example of the main control unit 111 will be explained using a block diagram of FIG. 2. Note that FIG. 2 shows a main configuration for carrying out the following explanation, the configuration not particularly mentioned in the following explanation is not shown in FIG. 2, and the explanation of the processing of such a configuration is also omitted.

In accordance with an exemplary embodiment, a control unit 251 controls operations of various functional units including each unit to be described below by executing processing using a computer program executable by a processor or data stored in a memory (not shown) and thereby controls the overall operation of the main control unit 111.

In accordance with an exemplary embodiment, a motor drive unit (MDU) 201 connects the probe 101 and rotates the imaging core. In the present embodiment, the MDU 201 is configured to output a pulse signal of 2048 pulses per revolution (pulse signal of 2048 pulses per one rotation of imaging core) as an encoder pulse signal.

In accordance with an exemplary embodiment, an encoder signal conversion unit 202 converts the encoder pulse signal from the MDU 201 into a pulse signal of an appropriate number of pulses (for example, a preset number of pulses among 512 pulses per revolution, 1024 pulses per revolution, and 2048 pulses per revolution) and outputs the converted pulse signal to a trigger signal generation unit 203.

In each sweep of wavelength sweeping light to be supplied to the imaging core, an optical unit 256 outputs a pulse signal indicating a timing of a predetermined state to the trigger signal generation unit 203 as a sweep signal. For example, a sweep signal may be generated by detecting light of a predetermined wavelength, or a sweep signal may be generated by detecting a position of a sweeping mechanism. In addition, a sweep signal may be generated based on a signal operating the sweeping mechanism. Furthermore, a reflected wave from the inside of the blood vessel is guided to the optical unit 256 via the MDU 201 and received by a photodiode (not shown) in the optical unit 256 as interference light interfered with the reference light in the optical unit 256. The interference light received by the photodiode in this manner is photoelectrically converted, amplified by an amplifier (not shown) in the optical unit 256, and then input into a demodulator (not shown) in the optical unit 256. In the demodulator, demodulation processing for extracting only a signal component of the interfered light is performed, and the output is input to the A/D (analog to digital) conversion unit 257 as an interference light signal. In the present embodiment, the optical unit 256 outputs a pulse signal (sweep signal) of 82 kHz to the trigger signal generation unit 203 and is set so as to generate an optical tomographic image of 512 lines per frame. Note that the sweep signals described in the disclosure are examples of the "pulse signal corresponding to an A line indicating a period of the light source".

In accordance with an exemplary embodiment, an electro-optic modulator (EOM) 205 switches the polarization state of the measurement light obtained from the light source as the light transmitted from the optical transceiver according to the signal from the trigger signal generation unit 203. Note that the polarization state of the light before being divided into the measurement light and the reference light may be switched.

In accordance with an exemplary embodiment, the trigger signal generation unit 203 determines an effective pulse from the pulse signal as a sweep signal based on the encoder pulse signal and generates a pulse signal including the effective pulse as a timing signal, for example, an AD trigger signal (i.e., analog digital trigger signal) indicating the timing to cause the A/D conversion unit 257 to perform A/D conversion. Furthermore, the trigger signal generation unit 203 generates a pulse signal which switches between high and low for every timing of the pulse of the AD trigger signal as a timing signal (modulation trigger signal) indicating the timing for causing the EOM 205 to switch the polarization state.

In accordance with an exemplary embodiment, the EOM 205 switches the polarization state of the measurement light based on the modulation trigger signal. In the present embodiment, the EOM 205 switches the polarization state of the measurement light to either a first polarization state or a second polarization state. When a rising edge of the pulse is detected in the modulation trigger signal (until a falling edge of the pulse is detected), the EOM 205 polarizes the polarization state of the measurement light to the first polarization state, and when the falling edge of the pulse is detected (until the next rising edge of pulse is detected), the EOM 205 polarizes the polarization state of the measurement light to the second polarization state. Note that the first polarization state and the second polarization state correspond to one and the other of two orthogonal polarization states, for example, on a Poincare sphere display, respectively. However, it is an example and not limited to this example.

Accordingly, the optical transceiver transmits the measurement light polarized to the first polarization state by the EOM 205 during a period from when the EOM 205 detects a rising edge of the pulse in the modulation trigger signal to when a falling edge of the pulse is detected, and the optical transceiver transmits the measurement light polarized to the second polarization state by the EOM 205 during a period from when the EOM 205 detects the falling edge of the pulse in the modulation trigger signal to when the rising edge of the next pulse is detected.

When a pulse in the AD trigger signal from the trigger signal generation unit 203 is detected, the A/D conversion unit 257 performs A/D conversion on the interference light signal received from the optical unit 256 as an interference light signal corresponding to the pulse and transmits the signal subjected to the A/D conversion to a signal processing unit 258. That is, the AD trigger signal is a pulse signal indicating a sampling start timing of the interference light signal.

In accordance with an exemplary embodiment, the signal processing unit 258 records the signal from the A/D conversion unit 257 as data in the memory and transmits the signal to an external device via a network line. For example, an index for specifying the polarization state may be assigned to a header of each A line data to be able to distinguish the switched polarization state of the data. Note that the output destination and the shape of the signal from the A/D conversion unit 257 are not limited to a specific output destination and form. In addition, the optical tomographic image may be generated based on the signal from the A/D conversion unit 257 and displayed on an LCD monitor 113 or output to the memory or an external device. Furthermore, the signal processing unit 258 may obtain polarization characteristics (such as phase difference or degree of polarization) from the signal of an Nth (N is an odd number equal to or larger than 1:1, 3, 5, . . . , and the number of lines per one frame of the optical tomographic image-1) line obtained from the A/D conversion unit 257 and the signal of an (N+1)th line adjacent to the nth line, may obtain the polarization characteristics of the biological tissue based on the polarization characteristics of a plurality of lines, and may output data indicating the obtained polarization characteristics to the memory or an external device.

Figure 3:
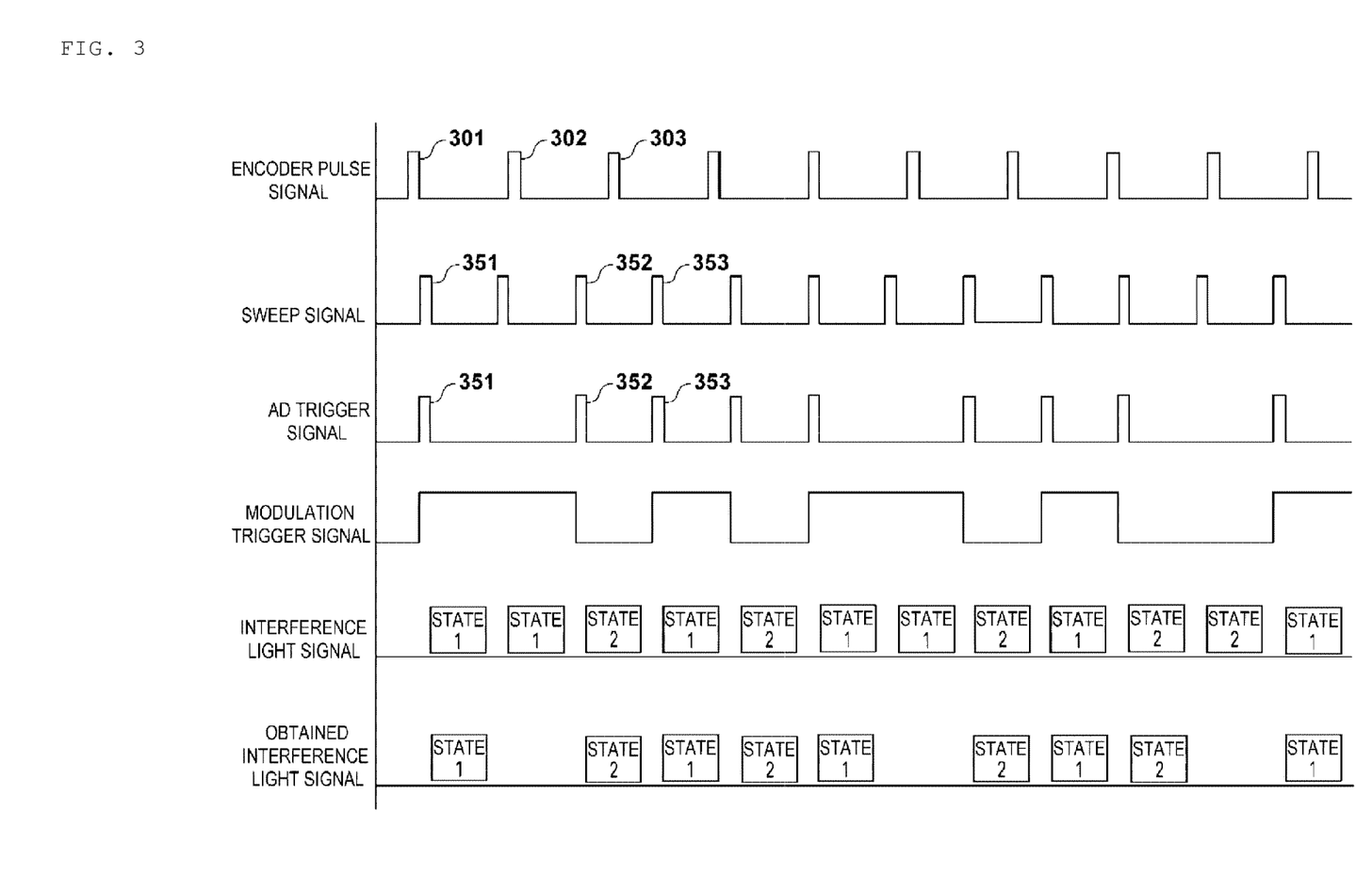
FIG. 3 is a diagram for explaining a specific operation example of a trigger signal generation unit, an EOM, and an A/D (analog-to-digital) conversion unit in accordance with an exemplary embodiment.

Next, the operation of the trigger signal generation unit 203, the EOM 205, and the A/D conversion unit 257 will be described in detail with reference to a specific example shown in FIG. 3. FIG. 3 shows an example of each of the above-described signals. In accordance with an exemplary embodiment, a time axis is provided from left to right in FIG. 3. In the case where each of the encoder pulse signal and the sweep signal as shown in FIG. 3 is output from the encoder signal conversion unit 202 and the optical unit 256, when a pulse of the encoder pulse signal is detected, the trigger signal generation unit 203 outputs a pulse detected from the sweep signal immediately after the detection to the A/D conversion unit 257 as an effective pulse. In the case of FIG. 3, when a pulse 301 is detected in the encoder pulse signal, a pulse 351 in the sweep signal immediately after the pulse 301 is output to the A/D conversion unit 257 as an effective pulse. Moreover, when a pulse 302 is detected in the encoder pulse signal, a pulse 352 in the sweep signal immediately after the pulse 302 is output to the A/D conversion unit 257 as an effective pulse. Furthermore, when a pulse 303 is detected in the encoder pulse signal, a pulse 353 in the sweep signal immediately after the pulse 303 is output to the A/D conversion unit 257 as an effective pulse. A pulse signal indicating an effective pulse train output from the trigger signal generation unit 203 to the A/D conversion unit 257 is shown as an AD trigger signal. As shown in FIG. 3, the AD trigger signal includes the above-described pulses from 351 to 353.

In accordance with an exemplary embodiment, the trigger signal generation unit 203 generates a pulse signal which switches between high and low each time a rising edge of an effective pulse is detected as a modulation trigger signal. In the case of FIG. 3, a modulation trigger signal which becomes high when a rising edge of the pulse 351 in the AD trigger signal is detected, becomes low when the rising edge of the next pulse 352 is detected, and becomes high when a rising edge of the next pulse 353 is detected is generated. When such a modulation trigger signal is input to the EOM 205, for example, the EOM 205 polarizes the measurement light to the first polarization state while the modulation trigger signal is high and polarizes the measurement light to the second polarization state while the modulation trigger signal is low.

As described above, when a pulse is detected in the AD trigger signal, the A/D conversion unit 257 performs A/D conversion on the interference light signal received from the optical unit 256 as an interference light signal corresponding to the pulse. In accordance with an exemplary embodiment, as shown in FIG. 3, while the modulation trigger signal is high, a signal of the interference light between the reflected light corresponding to the measurement light polarized in the first polarization state (state 1) and the reference light can be obtained. Therefore, when the pulse 351 is detected in the AD trigger signal, the A/D conversion unit 257 can perform the A/D conversion on the interference light signal received from the optical unit 256 as the corresponding interference light signal, that is, the signal of the interference light between the reflected light corresponding to the measurement light polarized in the first polarization state and the reference light. Furthermore, as shown in FIG. 3, while the modulation trigger signal is low, a signal of the interference light between the reflected light corresponding to the measurement light polarized in the second polarization state (state 2) and the reference light can be obtained. Therefore, when the pulse 352 is detected in the AD trigger signal, the A/D conversion unit 257 can perform A/D conversion on the interference light signal received from the optical unit 256 as the corresponding interference light signal, that is, the signal of the interference light between the reflected light corresponding to the measurement light polarized in the second polarization state and the reference light. Similarly, when the pulse 353 is detected in the AD trigger signal, the A/D conversion unit 257 can perform A/D conversion on the interference light signal received from the optical unit 256 as the corresponding interference light signal, that is, the signal of the interference light between the reflected light corresponding to the measurement light polarized in the first polarization state and the reference light.

As described above, according to the present embodiment, both the modulation trigger signal indicating the timing to instruct switching of the polarization state of the measurement light to the EOM 205 and the AD trigger signal indicating the timing causing the A/D conversion unit 257 to perform A/D conversion are generated corresponding to the effective pulse. Therefore, the interference light signal synchronized with the switching of the polarization state of the measurement light can be collected. When the change order of the polarization state is state 1→state 2→state 1→ . . . , the signal of the interference light can be obtained according to the change order of the polarization state as the signal of the interference light corresponding to the state 1→the signal of the interference light corresponding to the state 2→the signal of the interference light corresponding to the state 1→ . . . , for example.

Figure 4:
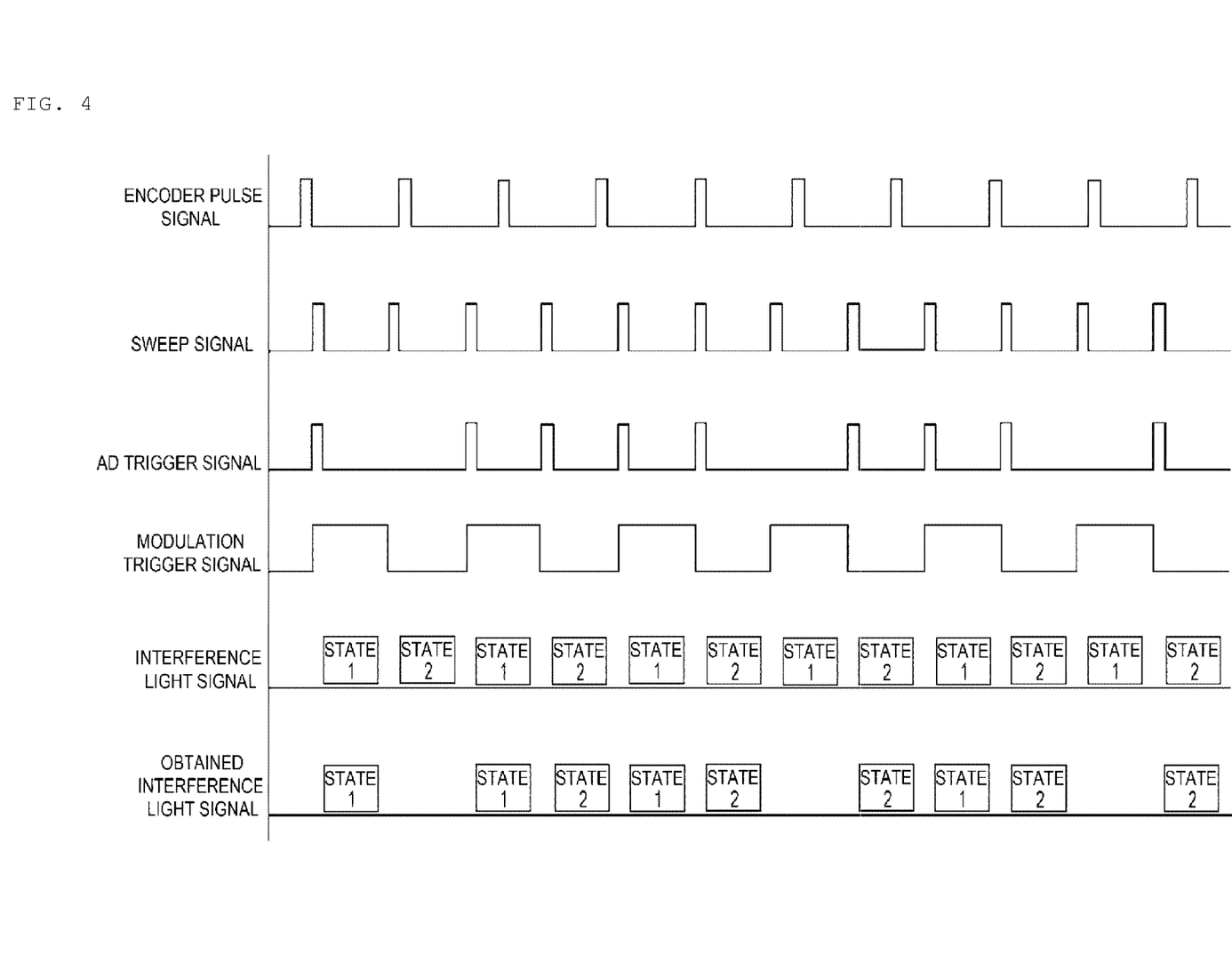
FIG. 4 is a diagram for explaining an alternative embodiment in accordance with an embodiment.

In accordance with an exemplary embodiment, the case where the trigger signal generation unit 203 generates the modulation trigger signal based on the sweep signal instead of the effective pulse (AD trigger signal) in the case of FIG. 3 will be described using FIG. 4.

In accordance with an exemplary embodiment, the trigger signal generation unit 203 generates a pulse signal which switches between high and low each time a pulse of the sweep signal is detected as the modulation trigger signal, and the EOM 205 polarizes the measurement light in the first polarization state during a period from the rising edge to the falling edge of the pulse in the modulation trigger signal and polarizes the measurement light in the second polarization state during a period from the falling edge to the rising edge of the pulse in the modulation trigger signal. In accordance with an exemplary embodiment, during the period from the rising edge to the falling edge of the pulse in the modulation trigger signal, the interference light signal of the interference light between the reflected light corresponding to the measurement light polarized in the first polarization state and the reference light is input to the A/D conversion unit 257, and during the period from the falling edge to the rising edge of the pulse, the interference light signal of the interference light between the reflected light corresponding to the measurement light polarized in the second polarization state and the reference light is input to the A/D conversion unit 257. However, since the A/D conversion unit 257 performs A/D conversion on the interference light signal corresponding to the pulse in the AD trigger signal, in the case of FIG. 4, the interference light signal corresponding to the switching order of the polarization state, such as the interference light signal corresponding to the state 1, the interference light signal corresponding to the state 2, the interference light signal corresponding to the state 1, . . . is input to the A/D conversion unit 257. However, it is not possible to perform A/D conversion on the interference light signal corresponding to the switching order of the polarization state such as the interference light signal corresponding to the state 1, the interference light signal corresponding to the state 1, the interference light signal corresponding to the state 2 . . . , when the A/D conversion is performed according to the AD trigger signal.

In the present embodiment, in the polarization sensitive OCT, even in the case where the A/D conversion is performed on the interference light signal corresponding to the effective pulse selected from the sweep signal based on the encoder pulse signal (due to the fact that the frequency of the light source is different from the operation frequency of the MDU 201), the interference light signals corresponding to the switching order of the polarization state of the measurement light can be collected.

Figure 5:
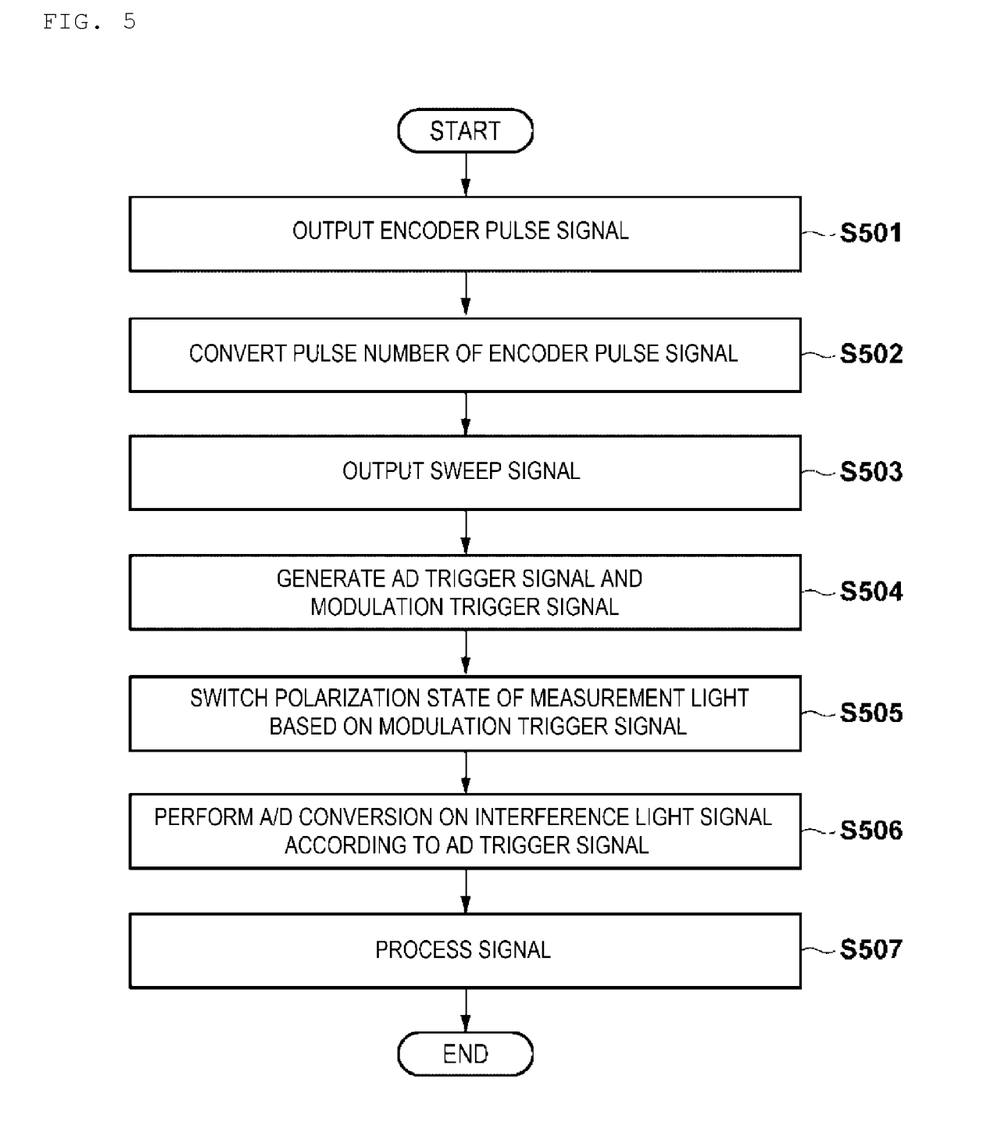
FIG. 5 is a flowchart of processing according to the configuration of the block diagram of FIG. 2.

The processing according to the configuration of the block diagram of FIG. 2 described above will be described with reference to the flowchart of FIG. 5.

In accordance with an exemplary embodiment, in step S501, the MDU 201 outputs a pulse signal of 2048 pulses per revolution to the encoder signal conversion unit 202 as an encoder pulse signal.

In step S502, the encoder signal conversion unit 202 converts the encoder pulse signal from the MDU 201 to a pulse signal of an appropriate number of pulses, and outputs the converted pulse signal to the trigger signal generation unit 203.

In step S503, the optical unit 256 outputs a pulse signal indicating the timing of the predetermined state of the wavelength sweeping light to the trigger signal generation unit 203 as a sweep signal.

In step S504, the trigger signal generation unit 203 determines an effective pulse from the pulse signal as a sweep signal based on the encoder pulse signal and generates a pulse signal including the effective pulse as an AD trigger signal. Furthermore, the trigger signal generation unit 203 generates a pulse signal, which switches between high and low for every timing of the pulse of the AD trigger signal as a modulation trigger signal.

In step S505, the EOM 205 switches the polarization state of the measurement light based on the modulation trigger signal.

In step S506, when a pulse is detected in the AD trigger signal from the trigger signal generation unit 203, the A/D conversion unit 257 performs A/D conversion on the interference light signal received from the optical unit 256 as the interference light signal corresponding to the pulse and transmits the signal subjected to the A/D conversion to the signal processing unit 258.

In step S507, the signal processing unit 258 processes the signal from the A/D conversion unit 257. As for the processing contents of the signal, various things are conceivable as described above, and it is not limited to specific processing contents.

Second Embodiment

In accordance with an exemplary embodiment, the encoder signal conversion unit 202, converting the signal into which pulse signal of 512 pulses per revolution, 1024 pulses per revolution, or 2048 pulses per revolution may be set, for example, as a user uses a mouse 114 while referring to a setting screen displayed on the LCD monitor 113. Moreover, the number of pulses may be set according to the number of revolutions and the number of pulses may be indirectly set by selecting the number of revolutions. In accordance with an exemplary embodiment, the method of setting the number of pulses to be converted is not limited to a specific setting method.

In addition, each numerical value used in the above description is merely an example used for concretely explaining the description, and the operation of the first and second embodiments is not limited to these numerical values.

In addition, the "sampling" used in the above-described embodiment may be interpreted as sampling a necessary signal out of the input signals, or may be interpreted as storing the input signal as an obtained signal and sampling a necessary signal from the stored signal.

In accordance with an exemplary embodiment, although the "pulse signal corresponding to the rotation of the imaging core" is described as being emitted from the MDU 201 in the above-described embodiment, the present disclosure is not limited to this. For example, the catheter itself may actively emit light.

In accordance with an exemplary embodiment, the encoder signal conversion unit 202 may be omitted.

The EOM 205 mentioned as a mechanism for switching the polarization state is not limited to optical products packaged in one available on the market.

A polarizer may be disposed in front of the EOM 205.

As described above, in each of the above processing, since the control unit 251 controls the operation of each unit by executing each processing using a computer program or data and the functions thereof are realized by the operations of the respective units, the computer program naturally falls within the scope of the present invention. Moreover, since the computer program is usually stored in a computer readable storage medium such as a CD-ROM or DVD-ROM and can be executed by setting it in a reading device (such as CD-ROM drive) of the computer and copying or install-ing it in the system, it is obvious that the computer readable storage medium falls within the scope of the present disclosure.

The present disclosure is not limited to the above-described embodiments, and various modifications and variations are possible without departing from the spirit and scope of the present disclosure. Accordingly, in order to publicize the scope of the present disclosure, the following claims attached.

The detailed description above describes to an image diagnostic technique. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An image diagnosis apparatus comprising:
    a motor drive unit configured to be connected to a probe, the probe being configured to rotatably accommodate an imaging core including an optical transceiver configured to transmit and receive light, the motor drive unit being configured to rotate the imaging core; and
    a processor configured to:
        determine an effective pulse based on a pulse signal corresponding to the rotation of the imaging core from a pulse signal corresponding to an A line indicating a period of a light source and for switching a polarization state of the light transmitted from the optical transceiver according to the effective pulse; and
        acquire a signal of interference light between the light received by the optical transceiver and reference light according to the effective pulse.

2. The image diagnosis apparatus according to claim 1, wherein the processor is configured to:
    determine, as the effective pulse, a pulse immediately after a pulse of the pulse signal corresponding to the rotation of the imaging core out of pulses of the pulse signal indicating the period of the light source.

3. The image diagnosis apparatus according to claim 1, wherein the processor is configured to:
    generate the pulse signal, which switches between a high and a low for every timing of the effective pulse, and switches the polarization state of the light transmitted from the optical transceiver according to the generated pulse signal.

4. The image diagnosis apparatus according to claim 1, wherein the processor is configured to:
    switch the polarization state of the light transmitted from the optical transceiver to one of polarization states orthogonal on a Poincare sphere display.

5. The image diagnosis apparatus according to claim 1, wherein the motor drive unit is configured to output a preset number of pulses per one rotation of the imaging core as the pulse signal; and
    an encoder signal conversion unit configured to convert the pulse signal from the motor drive unit into a converted pulse signal of a preset number of pulses, and outputs the converted pulse signal to a trigger signal generation unit.

6. The image diagnosis apparatus according to claim 5, comprising:

an optical unit configured to output the pulse signal indicating a timing of a predetermined state to the trigger signal generation unit as a sweep signal.

7. The image diagnosis apparatus according to claim 6, further comprising:
an electro-optic modulator configured to switch the polarization state of the measurement light obtained from the light source as the light transmitted from the optical transceiver according to the sweep signal from the trigger signal generation unit.

8. The image diagnosis apparatus according to claim 7, wherein the polarization state of the light is switched before being divided into the measurement light and the reference light.

9. The image diagnosis apparatus according to claim 1, comprising:
a trigger signal generation unit configured to determine the effective pulse from the pulse signal as a sweep signal based on the encoder pulse signal and generates a pulse signal including the effective pulse as a timing signal indicating the timing to cause the A/D (analog-to-digital) conversion unit to perform A/D conversion.

10. The image diagnosis apparatus according to claim 9, comprising:
an electro-optic modulator, and wherein the trigger signal generation unit is configured to generate a pulse signal which switches between a high and a low for every timing of the pulse of an AD trigger signal as a timing signal indicating the timing for causing the electro-optic modulator to switch the polarization state.

11. The image diagnosis apparatus according to claim 10, wherein the electro-optic modulator is configured to switch the polarization state of the measurement light based on the modulation trigger signal, and wherein the electro-optic modulator switches the polarization state of the measurement light to either a first polarization state or a second polarization state.

12. The image diagnosis apparatus according to claim 11, wherein a rising edge of the pulse is detected in the modulation trigger signal, the electro-optic modulator polarizes the polarization state of the measurement light to the first polarization state, and when the falling edge of the pulse is detected, the electro-optic modulator polarizes the polarization state of the measurement light to the second polarization state.

13. A method of controlling an image diagnosis apparatus having a motor drive unit configured to be connected to a probe, the probe configured to be rotatably accommodate an imaging core including an optical transceiver configured to transmit and receive light, and wherein the motor drive unit is configured to rotate the imaging core, the method comprising:
determining an effective pulse based on a pulse signal corresponding to the rotation of the imaging core from a pulse signal corresponding to an A line indicating a period of a light source and switching a polarization state of the light transmitted from the optical transceiver according to the effective pulse; and
acquiring a signal of interference light between the light received by the optical transceiver and reference light according to the effective pulse.

14. The method according to claim 13, further comprising:
determining, as the effective pulse, a pulse immediately after a pulse of the pulse signal corresponding to the rotation of the imaging core out of pulses of the pulse signal indicating the period of the light source.

15. The method according to claim 13, further comprising:
generating a pulse signal, which switches between a high and a low for every timing of the effective pulse, and switches the polarization state of the light transmitted from the optical transceiver according to the generated pulse signal.

16. The method according to claim 13, further comprising:
switching the polarization state of the light transmitted from the optical transceiver to one of polarization states orthogonal on a Poincare sphere display.

17. A non-transitory computer readable medium containing a computer program having computer readable code embodied to carry out a method of controlling an image diagnosis apparatus having a motor drive unit configured to be connected to a probe, the probe configured to be rotatably accommodate an imaging core including an optical transceiver configured to transmit and receive light, and wherein the motor drive unit is configured to rotate the imaging core, the method comprising:
determining an effective pulse based on a pulse signal corresponding to the rotation of the imaging core from a pulse signal corresponding to an A line indicating a period of a light source and switching a polarization state of the light transmitted from the optical transceiver according to the effective pulse; and
acquiring a signal of interference light between the light received by the optical transceiver and reference light according to the effective pulse.

18. The computer readable medium according to claim 17, further comprising:
determining, as the effective pulse, a pulse immediately after a pulse of the pulse signal corresponding to the rotation of the imaging core out of pulses of the pulse signal indicating the period of the light source.

19. The computer readable medium according to claim 17, further comprising:
generating a pulse signal, which switches between a high and a low for every timing of the effective pulse, and switches the polarization state of the light transmitted from the optical transceiver according to the generated pulse signal.

20. The computer readable medium according to claim 17, further comprising:
switching the polarization state of the light transmitted from the optical transceiver to one of polarization states orthogonal on a Poincare sphere display.

* * * * *